US011000332B2

(12) United States Patent
Dickhans et al.

(10) Patent No.: US 11,000,332 B2
(45) Date of Patent: May 11, 2021

(54) ABLATION CABLE ASSEMBLIES HAVING A LARGE DIAMETER COAXIAL FEED CABLE REDUCED TO A SMALL DIAMETER AT INTENDED SITE

(71) Applicant: COVIDIEN LP, Mansfield, MA (US)

(72) Inventors: William J. Dickhans, Longmont, CO (US); Joseph D. Brannan, Lyons, CO (US)

(73) Assignee: COVIDIEN LP, Mansfield, MA (US)

(*) Notice: Subject to any disclaimer, the term of this patent is extended or adjusted under 35 U.S.C. 154(b) by 160 days.

(21) Appl. No.: 15/642,495

(22) Filed: Jul. 6, 2017

(65) Prior Publication Data

US 2018/0036081 A1    Feb. 8, 2018

Related U.S. Application Data

(60) Provisional application No. 62/369,802, filed on Aug. 2, 2016.

(51) Int. Cl.
*A61B 18/18* (2006.01)
*A61B 18/00* (2006.01)

(52) U.S. Cl.
CPC ........... *A61B 18/1815* (2013.01); *A61B 2018/00577* (2013.01); *A61B 2018/1838* (2013.01);
(Continued)

(58) Field of Classification Search
CPC .......... A61B 18/1815; A61B 18/1492; A61B 2018/1892; A61B 2018/183; H01B 9/04;
(Continued)

(56) References Cited

U.S. PATENT DOCUMENTS

D223,367 S    4/1972  Kountz
D263,020 S    2/1982  Rau, III
(Continued)

FOREIGN PATENT DOCUMENTS

DE    390937 C      3/1924
DE    1099658 B     2/1961
(Continued)

OTHER PUBLICATIONS

European Search Report dated Jan. 4, 2018, issued in EP Appln. No. 17184178.
(Continued)

*Primary Examiner* — Thomas A Giuliani
*Assistant Examiner* — Christine A Dedoulis

(57) ABSTRACT

A microwave ablation cable assembly including a first coaxial cable having a first diameter, an inner conductor, an outer conductor and a dielectric formed between the inner and outer conductors, a second coaxial cable having a second diameter, and inner conductor, an outer conductor, and a dielectric formed between the inner and outer conductor, and a transition between the first and second coaxial cables having an inner conductor and outer conductor and a dielectric formed between the inner and outer conductors where the inner conductors of the first and second coaxial cables and the transition are in electrical communication and the outer conductors of the first and second coaxial cables and the transition are in electrical communication.

20 Claims, 1 Drawing Sheet

(52) U.S. Cl.
CPC ............... *A61B 2018/1861* (2013.01); *A61B 2018/1892* (2013.01)

(58) Field of Classification Search
CPC ... H01B 7/42; H01B 7/30; H01B 7/10; H01B 7/048; H01B 7/16; H01B 7/228; H01B 11/06; H01B 11/1033
See application file for complete search history.

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| 4,583,556 A | 4/1986 | Hines et al. | |
| D295,893 S | 5/1988 | Sharkany et al. | |
| D295,894 S | 5/1988 | Sharkany et al. | |
| D354,218 S | 1/1995 | Van de Peer | |
| 5,861,021 A * | 1/1999 | Thome | A61B 18/18 607/101 |
| D424,693 S | 5/2000 | Pruter | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| D487,039 S | 2/2004 | Webster et al. | |
| D496,997 S | 10/2004 | Dycus et al. | |
| D499,181 S | 11/2004 | Dycus et al. | |
| D525,361 S | 7/2006 | Hushka | |
| 7,101,369 B2 | 9/2006 | van der Welde | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| 7,311,703 B2 * | 12/2007 | Turovskiy | A61B 18/18 606/33 |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,875,024 B2 | 1/2011 | Turovskiy et al. | |
| D634,010 S | 3/2011 | DeCarlo | |
| D681,810 S | 5/2013 | DeCarlo | |
| 9,439,730 B2 | 9/2016 | Rossetto | |
| 2003/0088242 A1 * | 5/2003 | Prakash | A61B 18/18 606/33 |
| 2003/0195499 A1 * | 10/2003 | Prakash | A61B 18/14 606/33 |
| 2004/0049254 A1 | 3/2004 | Longo | |
| 2005/0015081 A1 | 1/2005 | Turovskiy et al. | |
| 2008/0294162 A1 * | 11/2008 | Rossetto | A61B 18/14 606/50 |
| 2010/0030207 A1 | 2/2010 | Hancock | |
| 2011/0077632 A1 | 3/2011 | Rossetto | |
| 2012/0172861 A1 | 7/2012 | Brannan | |
| 2014/0290830 A1 * | 10/2014 | Brannan | A61B 18/1815 156/86 |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1159926 A3 | 3/2003 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 56-161636 | 12/1981 |
| JP | 59-58933 | 4/1984 |
| JP | 5-5106 | 1/1993 |
| JP | 5-08933 | 2/1993 |
| JP | 05-40112 | 2/1993 |
| JP | 06343644 A | 12/1994 |
| JP | 07265328 A | 10/1995 |
| JP | H08-56955 | 5/1996 |
| JP | 08252263 A | 10/1996 |
| JP | 09000492 A | 1/1997 |
| JP | 9117456 | 5/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2002253569 A | 9/2002 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 1/1965 |
| SU | 401367 A1 | 10/1973 |

(56) References Cited

FOREIGN PATENT DOCUMENTS

| SU | 727201 A2 | 4/1980 |
|---|---|---|
| WO | 00/36985 A2 | 6/2000 |
| WO | 2010/035831 A1 | 4/2010 |

OTHER PUBLICATIONS

LigaSureTM Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'd Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H.H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.

(56) References Cited

OTHER PUBLICATIONS

Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With no Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite•Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, " LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

\* cited by examiner

ABLATION CABLE ASSEMBLIES HAVING A LARGE DIAMETER COAXIAL FEED CABLE REDUCED TO A SMALL DIAMETER AT INTENDED SITE

CROSS REFERENCE TO RELATED APPLICATION

The present application claims the benefit of and priority to U.S. Provisional Application Ser. No. 62/369,802, filed on Aug. 2, 2016, the entire contents of which are incorporated herein by reference.

BACKGROUND

1. Technical Field

The present disclosure relates to surgical instruments and, more specifically, to ablation cable assemblies.

2. Discussion of Related Art

Electromagnetic fields can be used to heat and destroy tumor cells. Treatment may involve inserting ablation antennas into tissues where cancerous tumors have been identified. Once the ablation antennas are properly positioned, the ablation antennas induce electromagnetic fields within the tissue surrounding the ablation antennas.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic fields to heat or ablate tissue.

Devices utilizing electromagnetic fields have been developed for a variety of uses and applications. Typically, apparatuses for use in ablation procedures include a power generation source, e.g., a microwave generator that functions as an energy source and an ablation antenna for directing energy to the target tissue. The generator and surgical instrument are typically operatively coupled by a cable assembly having a plurality of conductors for transmitting energy from the generator to the antenna, and for communicating control, feedback, and identification signals between the antenna and the generator.

The size of the active zone about an antenna is determined by the amount of energy which can be delivered to the antenna. With more energy delivered to the antenna, larger active zones can be generated. To maximize the energy delivered to the antenna, the diameter of a feed cable should be maximized along its length between the energy source and the antenna.

SUMMARY

The present disclosure relates generally to ablation cable assemblies having a feed cable with a large diameter portion that is reduced to a small diameter portion near the radiating section within the anatomy of a patient. By keeping the diameter of the feed cable large until it needs to be reduced the power handling of the ablation cable assembly can be increased when compared to ablation cable assemblies having a uniform diameter along the length thereof. In addition, the large diameter portion of the feed cable generates less heat than the small diameter coaxial feed cable. By generating less heat in the large diameter portion of the feed cable, cooling of the ablation cable assembly can be directed to the small diameter portion of the feed cable and the antenna which can increase the life and performance of the ablation cable assembly.

In aspects of the present disclosure, a microwave ablation cable assembly includes a first coaxial cable, a second coaxial cable, a transition, and a radiating section. The first coaxial cable has a first diameter, an inner conductor, an outer conductor, and a dielectric formed between the inner and outer conductors. The second coaxial cable has a second diameter, an inner conductor, an outer conductor, and a dielectric formed between the inner and outer conductors. The transition is positioned between the first and second coaxial cables and is positionable within the anatomy of a patient. The transition includes an inner conductor, an outer conductor, and a dielectric formed between the inner and outer conductors. The radiating section is in electrical communication with the first and second coaxial cables and the transition. The inner conductors of the first and second coaxial cables and the transition are in electrical communication with the outer conductors of the first and second coaxial cables and the transition are in electrical communication.

In aspects, the dielectric of the first coaxial cable has a larger diameter than the dielectric of the second coaxial cable. The dielectric of the transition can connect the dielectric of the first coaxial cable to the dielectric of the second coaxial cable. The cable assembly can include a sealing tube sealing connections between the dielectric of the first coaxial cable, the transition, and the second coaxial cable. The outer conductors of at least a portion of the first coaxial cable, the transition, and the second coaxial cable are formed over the sealing tube. The dielectric of the transition is shrunk fit over a portion of the inner conductor of the second coaxial cable to taper the diameter of the cable assembly from the first coaxial cable to the second coaxial cable.

In some aspects, the cable assembly includes an inner conductor transition that connects the inner conductor of the first coaxial cable and the inner conductor of the second coaxial cable. The inner conductor of the first coaxial cable is soldered to the inner conductor of the second coaxial cable.

In particular aspects, the second coaxial cable has a diameter in a range of about 0.004 inches to about 0.015 inches and the first coaxial cable has a diameter in a range of about 0.015 inches to about 0.150 inches.

In certain aspects, the radiating section includes a balun. The balun can include a balun dielectric and a balun conductor. The balun conductor can be electrically connected to the outer conductor of the second coaxial cable.

In some aspects, the radiating second includes at least one radiating portion. The radiating portion includes a proximal radiating section and a distal radiating section. The cable assembly can include a feed gap between the proximal and distal radiating sections.

Further, to the extent consistent, any of the aspects described herein may be used in conjunction with any or all of the other aspects described herein.

BRIEF DESCRIPTION OF THE DRAWINGS

Various aspects of the present disclosure are described herein below with reference to the drawings, which are incorporated in and constitute a part of this specification, wherein.

DETAILED DESCRIPTION

Figure 1:
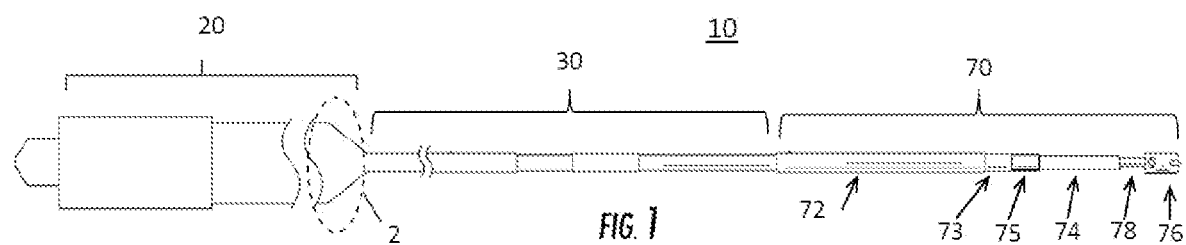
FIG. 1 is a side view of an ablation cable assembly 10 provided in accordance with the present disclosure.

This disclosure relates generally to an ablation cable assembly that having one or more transitions that are configured to be positionable within an anatomy of a patient to reduce the diameter of the ablation cable assembly based on the anatomy to access targeted tissue and/or to maintain an overall diameter despite the addition of structures, such as a balun, residing on the ablation cable assembly. Each transition is between a large diameter feed cable and a small diameter feed cable. By having a large and a small diameter feed cables, the ablation catheter assembly can deliver increased energy to tissue when compared to a feed cable having a constant diameter. In addition, the ablation catheter assembly can have an increased service life when compared to a feed cable having a constant diameter similar to the second diameter. The increased energy delivery and service life can be accomplished from a reduction of heating along the length of the large diameter portion of the feed cable.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

With reference to FIG. 1, an exemplary ablation cable assembly 10 is shown in accordance with the present disclosure. The ablation cable assembly 10 includes a large diameter feed cable 20, a small diameter feed cable 30, and a radiating section 70. Both the large diameter feed cable 20 and the small diameter feed cable 30 are coaxial cables as described in greater detail below. The radiating section 70 is comprised of a balun 72 (also sometimes referred to as a choke), a proximal radiating portion 74, a distal radiating portion 76 and a feedgap 78 located between the proximal and distal radiating sections. The balun 72 includes a balun conductor 73 shorted on its proximal end to the outer conductor 36 (FIG. 2) of the small diameter feed cable 30, and a balun dielectric 75 between the balun conductor 73 and the outer conductor 36. Though described here specifically as being a dipole antenna, one of skill in the art will recognize that a monopole antenna may also be utilized. In such a configuration only the distal 76 radiating is utilized.

The large diameter feed cable 20 may include a connector (not shown) configured to couple to a source of microwave energy and the radiating section 70 is configured to deliver microwave energy to tissue. Exemplary connectors and antennas are described in U.S. patent application Ser. No. 15/225,890, entitled "ABLATION CABLE ASSEMBLIES AND A METHOD OF MANUFACTURING THE SAME," U.S. Patent Publication No. 2014/0290830, and U.S. Pat. No. 9,247,992. The entire contents of each of these disclosures are hereby incorporated reference.

Though identified herein as large and small diameter feed cables 20 and 30, respectively, those of skill in the art will recognize that this is merely a designation of size relative to each other and not of their actual dimensions. In certain embodiments of the present disclosure, the small diameter feed cable 30 may have a nominal diameter of about 0.20 to about 0.060 inches (e.g., about 0.040 inches) and the large diameter feed cable 20 may have a nominal diameter of about 0.030 inches to 0.375 inches (e.g., about 0.125 inches) without departing from the scope of the present disclosure.

Figure 2:
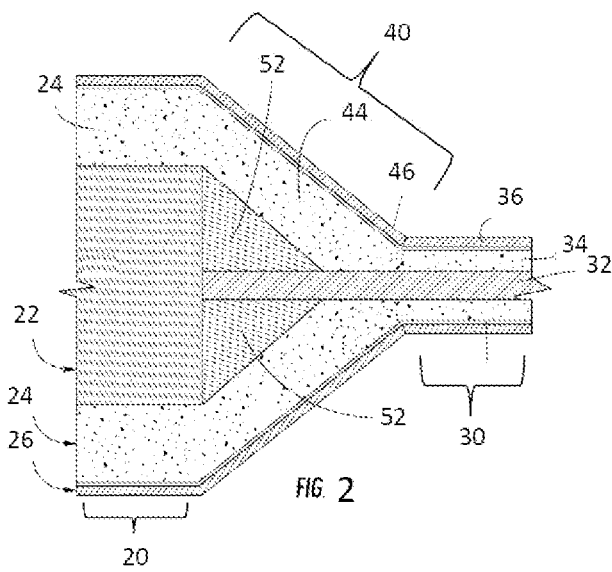
FIG. 2 is a cross-section of a transition portion the ablation cable assembly of FIG. 1.

As depicted with reference to FIGS. 1 and 2, the small diameter feed cable 30 electrically couples the large diameter feed cable 20 to the radiating portion 70. The large diameter feed cable 20 includes an inner conductor 22, an outer conductor 26, and a dielectric 24 between the inner and outer conductors 22, 26. The ablation cable assembly 10 includes a transition 40 from the large diameter feed cable 20 to the small diameter feed cable 30. The transition 40 includes a transition outer conductor 46, and a transition dielectric 44, and has a length of about 0.25 inches to about 2 inches. The transition outer conductor 46 is electrically coupled to the outer conductor 26 of the large diameter feed cable 20 and the outer conductor 36 of the small feed cable 30, and may in fact be formed as a single component with the outer conductors 26 and 36. For example outer conductors 26, 36, and 46 may be formed of a continuous woven braid capable of reducing its diameter without loss of electrical properties. Alternatively, the outer conductors 26, 36, and 46 may be soldered or crimped or otherwise mechanically secured to one another to ensure electrical connectivity to form an electrically continuous outer conductor along the length of the ablation cable assembly 10.

An inner conductor 32 of the small diameter feed cable 30 is electrically coupled to the inner conductor 22 of the large diameter feed cable 20. This electrical coupling may be accomplished via soldering with the solder forming an inner conductor transition 52 of the inner conductor. The inner conductor 32 has a smaller diameter than the inner conductor 22. The small diameter feed cable inner conductor 32 may have a nominal diameter of about 0.004 inches to about 0.015 inches (e.g., about 0.008 inches) and the large diameter feed cable inner conductor 22 may have a nominal diameter of about 0.015 inches to about 0.150 inches (e.g., about 0.060 inches) without departing from the scope of the present disclosure.

The transition dielectric 44 transitions between the dielectric 24 of the large diameter feed cable 20 and a dielectric 34 of the small diameter feed cable 30. The transition dielectric 44 may be formed from a shrinkable tube that is disposed over the inner conductor 22 of the large diameter feed cable 20 and upon application of heat shrinks to conform to the dimensions of the inner conductor 32 and inner conductor transition 52. Alternatively, the transition dielectric 44 may bond to the dielectrics 24 and 34. Further, the transition dielectric 44 and adjacent portions of dielectrics 24 and 34 may be covered by a sealing shrink tube 48 such that the joints between the transition dielectric 44 and the dielectrics 24 and 24 are sealed. The sealing shrink tube 48 is disposed between the outer conductors 26, 36, 46 and the dielectrics 24, 34, 44.

By having the large diameter feed cable 20 which is connectable to the energy source (not shown) the power handling and power transmission efficiency of the ablation catheter assembly 10 can be increased when compared to a traditional ablation catheter assembly having a constant diameter similar to a diameter of the small diameter feed cable 30 along its entire length. However, as will be appreciated, the small diameter feed cable 30 is necessary to reach desired locations within the body, whether percutaneously or endoscopically. One factor allowing for increased power handling of the ablation catheter assembly 10 may be a lower increase in temperature of the large diameter feed cable 20 allowing for improved cooling of the small diameter feed cable 30. For example, for an exemplary catheter assembly having a constant diameter over a 1 meter length, the efficiency of the catheter assembly is about 49 percent, whereas an exemplary ablation catheter assembly having a large diameter section reduced to an intermediate diameter section and then reduced to a small diameter section, which is approximately equal to the constant diameter, can have an efficiency of about 88 percent over the same 1 meter length.

The lengths and diameters of the large diameter feed cable 20 and the small diameter feed cable 30 may be determined by the targeted tissue and an access opening of a patient. For example, when the targeted tissue is within the lung and a bronchial access is being used, the large diameter feed cable 20 may be sized to pass through the mouth of a patient and into the bronchial pathways until the diameter of the bronchial pathways approaches the diameter of the large diameter feed cable 20. The transition to the small diameter feed cable 30 then permits continued access to the smaller bronchial pathways until the radiating section 70 is adjacent targeted tissue. A similar approach may be used for percutaneous applications, where the small diameter feed cable's length is only so long as necessary to achieve access to the treatment site, and all of the cable assembly which remains outside of the patient is formed of the large diameter feed cable.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A microwave ablation cable assembly, comprising: a first coaxial cable having a maximum outer diameter, an inner conductor, an outer conductor, and a dielectric formed between the inner and outer conductors; a second coaxial cable having a maximum outer diameter smaller than the maximum outer diameter of the first coaxial cable, an inner conductor, an outer conductor, and a dielectric formed between the inner and outer conductors, the inner conductor of the first coaxial cable having an outer diameter greater than an outer diameter of the inner conductor of the second coaxial cable; a transition disposed at a proximal end portion of the microwave ablation cable assembly and between the first and second coaxial cables, the transition reducing in diameter from the maximum outer diameter of the first coaxial cable to the maximum outer diameter of the second coaxial cable, and having an inner conductor, an outer conductor, and a dielectric formed between the inner and outer conductors, the inner conductor of the transition having a uniform outer diameter through the entire transition, wherein the inner conductor of the transition is coupled to the inner conductor of the first coaxial cable by an inner conductor transition extending through the transition; and a radiating section disposed distal to the second coaxial cable and in electrical communication with the first coaxial cable via the second coaxial cable and the transition, wherein the inner conductors of the first and second coaxial cables and the transition are in electrical communication and the outer conductors of the first and second coaxial cables and the transition are in electrical communication.

2. The cable assembly according to claim 1, wherein the dielectric of the transition connects the dielectric of the first coaxial cable to the dielectric of the second coaxial cable.

3. The cable assembly according to claim 2, further comprising a sealing tube sealing connections between the dielectric of the first coaxial cable, the transition, and the second coaxial cable.

4. The cable assembly according to claim 3, wherein the outer conductor of at least a portion of the first coaxial cable, the transition, and the second coaxial cable are formed over the sealing tube.

5. The cable assembly according to claim 2, wherein the dielectric of the transition is shrunk fit over a portion of the inner conductor of the second coaxial cable to taper the diameter of the transition from the first coaxial cable to the second coaxial cable.

6. The cable assembly according to claim 1, wherein the inner conductor of the first coaxial cable is soldered to the inner conductor of the second coaxial cable.

7. The cable assembly according to claim 1, wherein the maximum outer diameter of the second coaxial cable is in a range of about 0.004 inches to about 0.015 inches.

8. The cable assembly according to claim 1, wherein the maximum outer diameter of the first coaxial cable is in a range of about 0.015 inches to about 0.150 inches.

9. The cable assembly according to claim 1, wherein the radiating section further includes a balun having a maximum outer diameter smaller than the maximum outer diameter of the first coaxial cable.

10. The cable assembly according to claim 9, wherein the balun includes a balun dielectric and a balun conductor.

11. The cable assembly according to claim 10, wherein the balun conductor is electrically connected to the outer conductor of the second coaxial cable.

12. The cable assembly according to claim 1, wherein the radiating section includes a proximal radiating section and a distal radiating section.

13. The cable assembly according to claim 12, further comprising a feed gap between the proximal and distal radiating sections.

14. The cable assembly according to claim 1, wherein the inner conductor transition has an outer diameter greater than the outer diameter of the inner conductor of the second coaxial cable and the outer diameter of the inner conductor of the transition.

15. The cable assembly according to claim 1, wherein the outer diameter of the inner conductor of the second coaxial cable is uniform with the outer diameter of the inner conductor of the transition.

16. The cable assembly according to claim 1, wherein a distal end of the inner conductor of the first coaxial cable is disposed proximal to a proximal end of the transition.

17. A microwave ablation cable assembly, comprising: a first coaxial cable having a maximum outer diameter, the first coaxial cable having an inner conductor surrounded by an outer conductor; a second coaxial cable having a maximum outer diameter smaller than the maximum outer diameter of the first coaxial cable, the second coaxial cable having an inner conductor surrounded by an outer conductor, the inner conductor of the first coaxial cable having an outer diameter greater than an outer diameter of the inner conductor of the second coaxial cable; a transition disposed at a proximal end portion of the microwave ablation cable assembly and between the first and second coaxial cables, the transition reducing in diameter from the maximum outer diameter of the first coaxial cable to the maximum outer diameter of the second coaxial cable, the inner conductor of the second coaxial cable extending through the transition and coupled to the inner conductor of the first coaxial cable by an inner conductor transition extending through the transition, wherein the outer diameter of the inner conductor of the second coaxial cable is uniform through the entire transition; and a radiating section disposed distal to the second coaxial cable and in electrical communication with the first coaxial cable via the second coaxial cable.

18. The cable assembly according to claim 17, further comprising a balun having a maximum outer diameter smaller than the maximum outer diameter of the first coaxial cable.

19. The cable assembly according to claim 17, wherein the inner conductor transition has an outer diameter greater than the inner conductor of the second coaxial cable.

20. The cable assembly according to claim 17, wherein the outer diameter of the inner conductor of the second coaxial cable is uniform with the outer diameter of the inner conductor of the second coaxial cable extending through the transition.

\* \* \* \* \*